(12) United States Patent
Krause et al.

(10) Patent No.: US 6,447,518 B1
(45) Date of Patent: Sep. 10, 2002

(54) FLEXIBLE SHAFT COMPONENTS

(76) Inventors: William R. Krause, 820 Gilliams Mountain Rd., Charlottesville, VA (US) 22903; Garland U. Edwards, 13742 Village Ridge Dr., Midlothian, VA (US) 23113

( * ) Notice: Subject to any disclaimer, the term of this patent is extended or adjusted under 35 U.S.C. 154(b) by 0 days.

(21) Appl. No.: 09/557,607

(22) Filed: Apr. 25, 2000

Related U.S. Application Data

(63) Continuation-in-part of application No. 08/680,628, filed on Jul. 17, 1996, now Pat. No. 6,053,922.
(60) Provisional application No. 60/006,064, filed on Oct. 23, 1995, and provisional application No. 60/001,475, filed on Jul. 18, 1995.

(51) Int. Cl.[7] .............................................. A61B 17/16
(52) U.S. Cl. ........................................................ 606/80
(58) Field of Search ............................. 606/79, 80, 84, 606/85, 81, 96, 180; 464/54, 57, 58, 78, 59, 97; 408/199, 210

(56) References Cited

U.S. PATENT DOCUMENTS

| | | |
|---|---|---|
| 2,336,338 A | 12/1943 | Zublin |
| 2,344,277 A | 3/1944 | Zublin |
| 2,382,933 A | 8/1945 | Zublin |
| 2,515,365 A | 7/1950 | Zublin |
| 3,426,364 A | 2/1969 | Lumb |
| 3,753,301 A | 8/1973 | Daniel et al. |
| 3,753,302 A | 8/1973 | Daniel |
| 3,754,338 A | 8/1973 | Culver |
| 3,762,070 A | 10/1973 | Culver |
| 3,962,801 A | 6/1976 | Gonzalez |
| 4,401,112 A | 8/1983 | Rezaian |
| 4,554,914 A | 11/1985 | Kapp et al. |
| 4,599,086 A | 7/1986 | Doty |
| 4,932,975 A | 6/1990 | Main et al. |
| 5,147,404 A | 9/1992 | Downey |
| 5,152,692 A | 10/1992 | Richard |
| 5,192,327 A | 3/1993 | Brantigan |
| 5,488,761 A | * 2/1996 | Leone ......................... 29/2.25 |
| 5,571,192 A | 11/1996 | Schonhoffer |

* cited by examiner

*Primary Examiner*—David O. Reip
(74) *Attorney, Agent, or Firm*—Sheldon H. Parker

(57) ABSTRACT

An improved flexible shaft used in the reaming of the medullary space in bones is described. The shaft is comprised of a solid element with a longitudinal bore the entire length and an appropriately formed slot which extends spirally around the shaft either continuously or segmentally. Attached to the shaft's opposite ends respectively, are a cutting head and a means of connecting the shaft to a driving mechanism. Additionally, an improved anthropomorphic spinal element and vertebral body replacement implant are described. The anthropomorphic spinal element is composed of a solid element with a longitudinal bore and an appropriately formed slot that extends spirally around the shaft either continuously or segmentally and is completely or partially filled with an elastomeric material. The vertebral body replacement implant is composed of a suitable implant material with a longitudinal bore the entire length and an appropriately formed slot which extends spirally around the shaft either continuously or segmentally. Attached to the central section's opposite ends are a means of attachment to the adjacent vertebra allowing for height and angular adjustment.

3 Claims, 10 Drawing Sheets

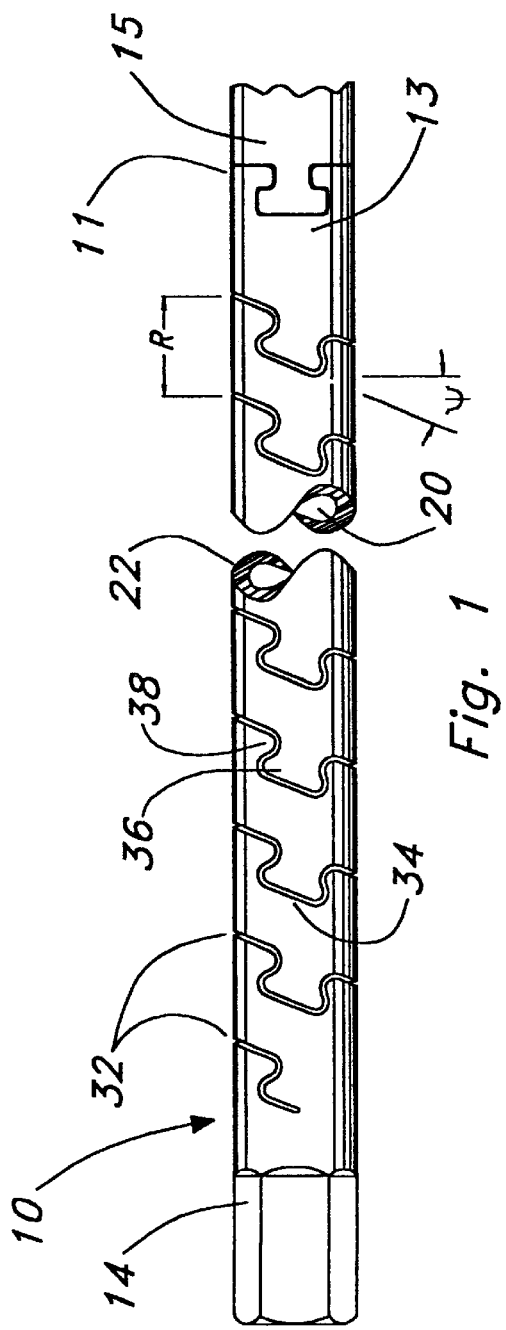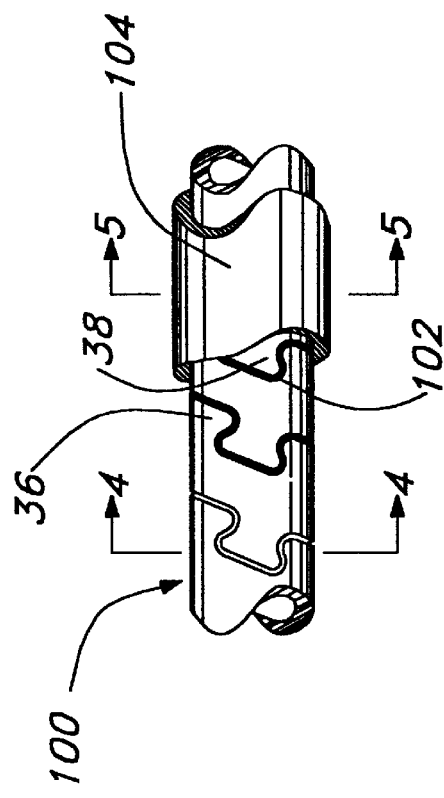

FLEXIBLE SHAFT COMPONENTS

CROSS REFERENCE TO RELATED APPLICATIONS

This application is a continuation in part of U.S. application Ser. No. 08/680,628 filed Jul. 17, 1996, now U.S. Pat. No. 6,053,922, which claims the benefits under 35 U.S.C. 119(e) of provisional patent application, Ser. No. 60/006,064 filed Oct. 23, 1995 and provisional application Ser. No. 60/001,475 filed Jul. 18, 1995, the subject matters of which are incorporated herein, by reference, as though recited in full.

BACKGROUND OF THE INVENTION

1. Field of the Invention

This invention relates to flexible shafts and coupling designs that provide a greater control and can be adapted to an improved flexible shaft for the transmission of rotary motion and power around, over or under obstacles, i.e. reaming the medullary canal of bones, vertebral body replacement implant, as well as forming a segment of the spinal column of anthropomorphic dummies.

2. Brief Description of the Prior Art

Flexible Shafts

Flexible shafts and couplings are used to transmit rotary power between a power source and a driven part in a curvilinear manner. These shafts are used when there is little or no accurate alignment between the power source and the driven part; when the path between the power source and the driven part is blocked or is in an environment or position which would not allow the power source; for the connection or driving of components which have relative motions; and to dampen and absorb vibration both from the drive unit and the driven tool.

A flexible shaft generally consists of rotating shaft with end fittings for attachment to mating parts, typically a power source and the driven part, as depicted in FIG. 3 of U.S. Pat. No. 4,646,738, Suhner catalog at page 6, and the S.S. White Technologies Inc. catalog, page 4, (1994). A protective outer casing can be used to protect the shaft when necessary. Flexible shafts are used in numerous applications anywhere the transmission of rotary power is necessary and a straight unobstructed path is unavailable, as depicted in the S.S. White Technologies Inc. catalog, page 5 and Suhner at page 6. Flexible shafts have been used in children's toys to aerospace applications. Examples of the usage of flexible shafts have been presented in the articles "New Twists for Flexible Shafts" (Machine Design, Sep. 7, 1989), in particular pages as illustrated on pages 145 and 146, and "Flexible Shafts Make Obstacles Disappear" (Power Transmission Design, July, 1993), in particular FIG. 1. One example cited was a safety valve, located 30 ft. off the ground and not readily accessible, that had to be operated on a daily basis to remain operable, but was not exercised as regularly as required due to the difficulty in reaching it. With the installation of a flexible shaft from the valve to floor level, personnel were able to operate the valve regularly and verify its proper function. Flexible shafts are used on aircraft to raise and lower wing flaps, slats, and leading and trailing edges. Stainless steel flexible shafts allow surgeons greater maneuverability with bone cutting and shaping tools. Flexible shafts are also used extensively to compensate for less than perfect alignment between a driver and a driven component. The limitation for the use of flexible shafts are limitless and is only limited by the torque capabilities of the shaft.

Heretofore, flexible shafts and couplings available for power transmission consisted of single or multiple wires wound over a central drive core or a hollow core, as illustrated in U.S. Pat. No. 5,108,411, FIG. 2, and as depicted in the Suhner publication, pages 15 and 16. The number of wires per layer and the number of layers will vary according to the application and requirements for either unidirectional or bi-directional torque power transmission. Typically wire wound flexible shafts are designed and manufactured to be operated in only one direction of rotation; either clockwise or counter clockwise, when viewed from the driving end. They are designed to maximize the torque carrying capabilities for the direction of rotation for which they were designed. The performance of a unidirectional shaft operated in the reverse direction is significantly less than the intended performance levels.

A specific application of flexible shafts is with flexible medullary canal reamers. Medullary canal reamers are used to enlarge the medullary canal of bones in preparation for the insertion of prosthetic components, such as a total hip prosthesis, the insertion of fracture reduction and fixation devices, such as intramedullary nails, performing an intramedullary osteotomy, the insertion of a plug to preclude bone cement from migrating while in its viscous state, stimulating bone growth, and for other purposes. Since the medullary canal is irregular in internal diameter and configuration from end to end it is preferred by the surgeon to enlarge the medullary canal to a more uniform diameter or to a diameter that will allow passage or insertion of the intended device. Because the shafts of long bones are bent or curved along their longitudinal axes, flexible shafts that can bend to follow this naturally curved path while transmitting the necessary torque required to cut the bone are necessary.

Should a straight, rigid, or inflexible shaft be used in the reaming process to enlarge the canal, there is considerable likelihood that the reamer will not follow the natural curvature of the bone, will not remove the desired amount of bone and will not produce a uniform internal diameter. In addition, should a straight, rigid reamer be used, there is a high degree of likelihood that the reamer will jam, cause excessive bone removal or penetrate the outer integrity of the bone. For this reason, medullary canals are almost always prepared with reamers having a flexible shaft. Flexible medullary reamers are of such design that utilizes a central bore intended to receive a long, small diameter guide rod or wire that is initially inserted into the medullary canal. The guide wire or rod establishes a track for the advancing reamer. However, the use of a flexible reamer does not preclude the problem of jamming or reamer stoppage when the cutting head of the reamer gets caught by the bony structure and does not turn. A jammed cutting head may be extremely difficult, if not impossible to dislodge or remove without further violation of the involved bone or breakage of the reaming device. The preferred method to dislodge the reamer would be to reverse the reamer. However, the design of the most widely used devices prevent the reversal of the reamer without destruction of the flexible shaft.

Heretofore, the flexible medullary shaft reamers available to the orthopedic surgeon are of three types: (i) a shaft with a plurality of parallel flexible elements or rods joined together at opposite ends by means of a welded of soldered connection, (ii) a shaft comprised of a spiral or helically wound metal wire(s) or strip(s), and (iii) a shaft comprised of a series of inter-engaged links, assembled over a guide rod.

The first distinct type of flexible medullary reamer (i) embodies a plurality of parallel, flexible elements joined together at opposite ends. A disadvantage of this shaft occurs during usage as the reamer rotates causing the elements to become twisted and thereby to become more rigid and reduce the shaft's flexibility. Another disadvantage of said reamer is the shaft's tendency, as it rotates but is not yet fully within the confines of the medullary canal, to tear tissue from underlying structures as the individual elements are torsionally loaded and unloaded, thereby enlarging and contracting the spaces between the individual wires to trap uninvolved tissue and tearing them free.

Another disadvantage of said flexible reamer occurs during insertion of the reamer over the guide rod. The central bore is intended to receive the small diameter guide rod. Except at its respective ends, this reamer lacks a well defined and bordered central bore. Therefore it is difficult to prevent the guide rod from exiting the reamer in the area of the free standing elements during the insertion of the guide wire. A further disadvantage of this flexible shaft is the inefficient transfer of energy from the power source to the cutting head that is caused by the twisting and wrapping together of the individual elements as the reamer is rotated. Another disadvantage of this type of reamer is that it is extremely noisy during operation due to the multiple elements hitting one another during the rotation.

The second distinct type of flexible medullary reamer (ii) consists of spiral or helically wound metal wires or strips. This is the most widely used flexible shaft for intramedullary reaming. The major disadvantage of this reamer design is that it can only be operated in the forward mode of operation. If the cutter becomes jammed and the surgeon reverses the reamer to dislodge the cutter or to facilitate removal, the shaft unwinds, thus rendering the reamer permanently deformed, unusable, and unrepairable. A further disadvantage of this medullary reamer is that the tensional load to which it is subjected when in use results in poor power transfer and varying degrees of distortion of said shaft. If the power source providing the rotational energy to the reamer is great enough, the coils can tighten sufficiently to adversely affect the structural integrity of the shaft and cause the shaft to permanently deform into a helical shape. A further disadvantage of this type of reamer is the inability to clean the shaft and the cavities within the helically wound strips of surgical debris after the operation for the prevention of cross contamination between patients. If infectious blood or body fluids infiltrates the mechanism of the device, it is extremely difficult to remove and clean.

The third distinct type of flexible shaft (iii) consists of a series of inter-engaged links assembled over a guide wire. A distinct disadvantage of this design is during usage and inter-changing the cutting head. The current usage of this design dictates that the links are held together by a longitudinal guide wire over which the linkages are assembled. In order to change the cutting head, a flexible tube must be inserted through the central bore of the linkages, and the assembled links must be taken off the centralizing guide wire. In the process linkages frequently become unassembled and require the surgeon to reassemble the linkages.

U.S. Pat. No. 5,488,761 to Leone, shows prior art spiral wound flexible shafts using a single shaft and a pair of reverse wound shafts. The patent also discloses materials of construction or the shaft and a mechanism for cleaning the slot, after it is cutting. Alternate cutting technologies are also disclosed.

The prior art is depicted in Matthews, U.S. Pat. No. 4,706,659 which show two modifications of prior art devices, in FIGS. 1 and 2. The device of Matthews is loosely related to the present invention in that it is a mechanism for providing a flexible connecting shaft for an intramedullary reamer. While the proposed solution to the problem is different from that of the present invention, the patent discloses the importance of a flexible connection and discloses reamer structures. The disclosure of Matthews 4,706, 659 is incorporated by reference herein, as though recited in full.

U.S. Pat. No. 4,751,922 (DiPietropolo) also shows the importance of flexible medullary reamers and explains some of the prior art problems. The patent also discloses the use of a hollow core 2, for receiving a guide pin. U.S. Pat. No. 5,122,134 (Borzone et al) is incorporated by reference as though recited in full and is noted to disclose in FIG. 5, the use of a guide pin 55.

FIG. 1 of Zublin, 2,515,365 illustrates a flexible drill pipe for use in the drilling of well bores. Additional Zublin patents include U.S. Pat. Nos. 2,515,366, 2,382,933, 2,336, 338 and 2,344,277. The drill pipe is a helically slotted flexible drill pipe having a slot varying from 3/32of an inch (0.0938") to 5/32 of an inch (0.1563") in width and having a pitch of the spiral of about nine inches for a four and one-half inch diameter drill pipe (helix angle of 32.48 deg). Zublin indicates that the described flexible resilient drill pipe has the capacity to bend into a curve of an eighteen foot diameter utilizing a repeating "dovetail" pattern of over six cycles per revolution, for use with four and one half inch diameter drill pipe. In the instant invention, it has been found that shafts of one inch or less require the use of a helix angle of approximately one half that described by Zublin and that the number of repeating cycles of the interlocking pattern is less than the shown six cycles per revolution. For the smallest of flexible shafts describe, the use of about two pattern repetitions (cycles) per spiral revolution is more appropriate.

Spinal Element

The disclosed technology can also provide a tubular structure with certain stiffness characteristics that have the controllability to be varied dependent upon the application. An example of this would be in automotive and aircraft crash test evaluation and aircraft ejection seat response. In applications where the test is aimed at determine a human response, it is desirable to provide a spinal element to be inserted into a test manikin which has the biofidele response of the human spinal column or segment.

Various spine mechanisms have been developed for anthropomorphic test devices (ATD). The devices can be divided into vertically stacked vertebral simulating members, U.S. Pat. Nos. 3,754,338, 3,753,301, 3,753,302, 3,762,070, and 3,962,801 or a single unit member typically composed of a solid rubber beam, U.S. Pat. No. 5,152,692.

Richards (5,152,692) discloses a biofidelic manikin neck comprising a butyl rubber beam inserted between an aluminum base and an aluminum top, with a stainless steel cable assembly in the middle of the beam connecting the top to the base. In an embodiment of the invention, a pivot joint is bolted to a lug in the neck top, with the joint being attached to a head mounting plate to provide head nodding action. An outer cylinder, comprised of a thick sheet of butyl rubber attached vertically around the head mounting plate and the neck base, allows the head moment to respond to the angle between the head and the torso. A second embodiment of the invention uses a torsion release swivel joint instead of a pivot joint with additional strips of butyl rubber to stiffen the neck response. A third preferred embodiment uses a rectangular inner beam, and a roughly oval-shaped outer support structure.

Vertebral Body Replacement Implant

In situations when a vertebra is broken, crushed or diseased, it is frequently necessary to ablate the body of the crushed or diseased vertebra. In order, however to prevent the spinal column from collapsing with damage to the spinal cord running in the vertebral foramen forward of the vertebral body, it is necessary to employ a spacer. The spacer is braced vertically between the bodies of the adjacent vertebrae, maintaining them at the desired separation distance. A substitute vertebra with biofidelic properties would provide the optimum replacement.

Various implants have been developed to address structural failure of various parts of the spinal column. The prior art with respect to spinal column implants falls into two general categories: intervertebral disc prostheses, and rigid vertebral body prostheses.

Vertebral body prostheses have been disclosed in U.S. Pat. Nos. such as 3,426,364, 4,401,112, 4,554,914, 4,599,086, 4,932,975, and 5,571,192. The referenced patents typically are composed of a rigid, height adjustable device and are typically a threaded cylinder or turnbuckle mechanism with anchoring plates. Another type of replacement device is composed of individual elements that are sized and adapted to be fitted together to provide support to the adjacent vertebra. This type of device has been described in U.S. Pat. Nos. 5,147,404 and 5,192,327.

The devices presented in the foregoing patents are intended for situations where it is necessary to remove a vertebral body. That, in turn, requires the resection of adjacent intervertebral discs. A problem common to all of such prior devices is that while they adequately provide the structure of the removed vertebral body, they fail to provide the flexibility of the removed intervertebral discs.

The disclosed invention provides a cylindrical device, containing a helical pattern than, when adapted to the end use, provides a flexible column that can be used in a variety of applications. When adapted for use with as flexible shaft, the device will flex, bend or curve to follow the natural intramedullary canal of the bone while transmitting reaming torque. When adapted for use as a vertebral body replacement implant, the device provides axial, bending, and torsional stiffness can provide the mechanical characteristics of the vertebral body and disc specified for replacement. The axial, bending and torsional stiffness can be modified for use as an anthropomorphic spine unit that faithfully reproduces human-like responses in ejection seat and vehicle crash tests, enabling researchers to identify and eliminate the cause of spinal injuries.

These and other features, advantages and aspects of the present invention will be better understood with reference to the following detailed description of the preferred embodiments when read in conjunction with the appended drawing figures.

SUMMARY OF THE INVENTION

The present invention overcomes the deficiencies and problems evident in the prior art as described herein above by combining the following features into an integral, longitudinally flexible and torsionally inflexible shaft. The disclosed flexible shaft provides for the transmission of rotary power from a drive power unit to a driven unit. The driven unit can be a drill bit, a surgical reamer, a pump, or any similar device. The flexible shaft is an elongated tubular member of substantial wall thickness. The diameter of the shaft is preferably in the range from about 0.15 inch to about 4.00 inch. The ratio of the diameter of the inside diameter of the shaft to the outside diameter of the shaft is advantageously in the range from about 1:1.2 to about 1:3, and preferably is in the range from about 1:1.3 to about 1:4. The thinner the wall of the shaft, the more critical is the configuration of the slot.

A slot of substantial length and width extends in a generally helical path, either continuously or intermittently, around and along the tubular member. Advantageously, the slot is cut at an angle normal to the shaft using a computer controlled cutting technique such as laser cutting, water jet cutting, milling or other means. The slot follows a serpentine path along the helical path generally around and along the tubular member, corresponding generally to the form of a signal wave on a carrier wave, that is, an amplitude modulated carrier wave. Additionally, this slot may be cut at an angle to the normal so as to provide an undercut slot, preferably the angle is in the range from about 30 to about 45 degrees from the normal.

A plurality of slots, can also be employed thereby increasing the flexibility of the shaft, relative to a shaft having a single slot of identical pattern. The serpentine path forms a plurality of teeth and complimentary recesses on opposite sides of the slot. The slot has sufficient width to form an unbound joint permitting limited movement in any direction between the teeth and the recesses, thereby providing limited flexibility in all directions upon application of tensile, compressive, and/or torsion forces to said shaft.

Different degrees of flexibility along the length of said shaft can be achieved by having the pitch of the helical slot vary along the length of the shaft. The varied flexibility corresponds to the variation in the pitch of the helical slot. The helical path can have a helix angle in the range of about 10 degrees to about 45 degrees, and the helix angle can be varied along the length of the shaft to produce correspondingly varied flexibility. Alternatively, the width of the helical slot can vary along the length of the shaft to provide the varied flexibility. Advantageously, the width of the slot is preferably in the range from about 0.005 inch to 0.075 inch. Preferably the width of the slot is in the range from about 0.01 to about 0.05 inch. The rigidity of the flexible shaft can be achieved through the design of the slot pattern, thereby enabling the use of thinner walls than would otherwise be require to produce equivalent rigidity. In a preferred embodiment, the ratio of the amplitude of the serpentine path to the pitch of the slot is in the range from greater than 0.1 to about 0.5.

The slot can be filled with a resilient material, partially or entirely along the path of the slot. The resilient material can be an elastomer, such as urethane or a silicone compound, which can be of sufficient thickness to fill the slot and to encapsulate the entire shaft thus forming an elastomer enclosed member.

In a preferred embodiment the driven unit is a medullary canal reamer, for use in reaming the medullary canal of bones. In this application, the foregoing slot patterns and shaft dimensions, are particularly critical.

Preferably, the flexible shaft, is formed by laser cutting an elongated tubular member of substantial wall thickness, to form the slot around and along the tubular member. The serpentine path can form of a generally sinusoidal wave superimposed on a helical wave. Preferably, the sinusoidal wave forms dovetail-like teeth, which have a narrow base region and an anterior region which is wider than the base region. Thus, adjacent teeth interlock.

Anthropomorphic Spine Unit

This embodiment provides an apparatus for protecting occupants of vehicles in crashes or in sudden positive or negative accelerations. More specifically, it relates to a spinal unit for use in anthropomorphic dummies or manikins intended to simulate human occupants in testing for the effectiveness of protective equipment.

The development of test dummies demonstrates that they have been designed primarily for applications in automobiles. One of the main concerns in automobile crashes is the response of the torso to impacts from the forward and lateral directions. Ejection seat manikins, however, are subjected to sudden vertical accelerations as well as to horizontal acceleration. The manikins are much more sophisticated representations of the human body and have been developed specifically for ejection seat testing by the Armed Services. Although the accuracy of the test results are dependent on the biofidelity of the ATD to provide the response that of a human, the current spinal units incorporated into either automobile crash dummies or aircraft manikins do not faithfully model the motion of the human spine. Therefore a spinal unit incorporated in an ATD that has the mechanical properties of the human spine segment (lumbar, thoracic or cervical) will provide improved test results and evaluation of restraint systems.

BRIEF DESCRIPTION OF THE DRAWINGS

These and other objects, features, advantages and aspects of the present invention will be better understood with reference to the following detailed description of the preferred embodiments when read in conjunction with the appended drawing figures.

FIG. 1 is a schematic representation of a flexible shaft of the present invention;

FIG. 2 is a schematic representation of the spiral slit of FIG. 1, showing coated and uncoated regions;

DETAILED DESCRIPTION OF THE PREFERRED EMBODIMENTS

Figure 5:
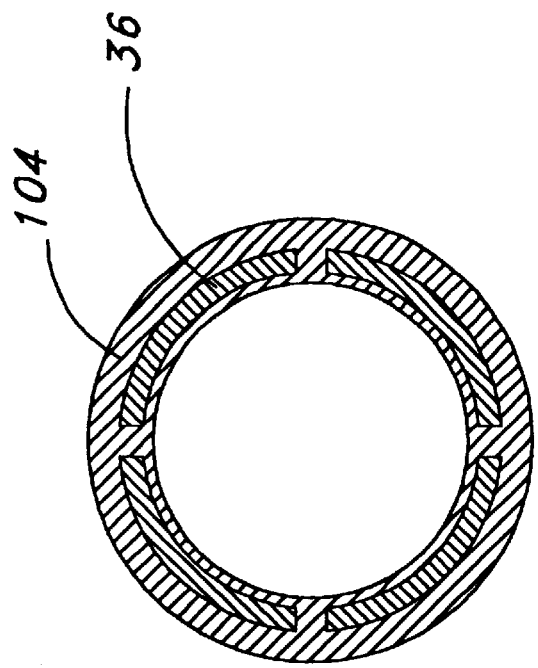
FIG. 5 is a schematic representation of a flexible cable with a resilient filler in a portion of the slot.

The disclosed device uses a helical pattern cut into a cylinder to provide flexibility. By altering the ratio and pattern of cut to uncut portions of the helix, the flexibility of the cylinder is controlled. The disclosed device can be used to create a flexible shaft for the purpose of reaming the medullary canal of bones, as well as a vertebra implant for one or more vertebra or s a spinal unit for anthropomorphic test devices.

DEFINITIONS AND TERMS

The term slot as used herein, is defined in the American Heritage Dictionary, 3rd Edition, Copyright 1994, as follows:

The terms slit and slot are used interchangeably, consistent with their definitions, as follows:

slot n. 1. A narrow opening; a groove or slit: a slot for coins in a vending machine; a mail slot.

2. A gap between a main and an auxiliary airfoil to provide space for airflow and facilitate the smooth passage of air over the wing.

The term pitch as used herein, is defined in the American Heritage Dictionary, 3rd Edition, Copyright 1994, as follows:

pitch–n. 1. The distance traveled by a machine screw in one revolution.

2. The distance between two corresponding points on adjacent screw threads or gear teeth.

The term helix angle, angle θ in FIG. 1, as used herein, shall define the angle formed between the plane perpendicular to the longitudinal axis of the shaft and the helical path of the spiral along the shaft. The term helix angle can also be defined mathematically as the arc tangent of the pitch of the helix divided by the circumference of the shaft.

As used herein the term serpentine refers to the undulations of the cut in any geometric configuration whether it is dovetailed, mating or winding fashion.

The terms used herein are intended to have their customary meanings as set forth in the American Heritage Dictionary, $3^{rd}$ Edition, Copyright 1994.

Cycle—1. An interval of time during which a characteristic, often regularly repeated event or sequence of events occurs: Sunspots increase and decrease in intensity in an 11-year cycle.

2a. A single complete execution of a periodically repeated phenomenon: A year constitutes a cycle of the seasons.

2b. A periodically repeated sequence of events: cycle includes two halves of the sine-wave like undulation of the slot path.

Spiral 1a. A curve on a plane that winds around a fixed center point at a continuously increasing or decreasing distance from the point.

1b. A three-dimensional curve that turns around an axis at a constant or continuously varying distance while moving parallel to the axis; a helix.

1c. Something having the form of such a curve: a spiral of black smoke.

2. Printing. A spiral binding.

3. Course or flight path of an object rotating on its longitudinal axis.

4. A continuously accelerating increase or decrease: the wage-price spiral. Spiral (adj.)

1. Of or resembling a spiral.

2. Circling around a center at a continuously increasing or decreasing distance.

3. Coiling around an axis in a constantly changing series of planes; helical.

The term amplitude, as used herein the maximum absolute value of the periodically varying quantity of the slot 30.

The spiral is more explicitly a helix-like, in that it is a three-dimensional curve that lies on a cylinder, so that its angle to a plane perpendicular to the axis is constant. However, along the length of the shaft, the helix angle may vary so as to impart changes in flexibility to the overall shaft. Using an electronics analogy, the helix can be viewed as a carrier wave with the slot following the path of the modulation of the carrier wave. The teeth or interlocking regions of the cycle, form a ratchet-like structure, in that one set of teeth engage the other set of sloping teeth, permitting motion in one direction only.

The term frequency, the number of times a specified phenomenon occurs within a specified interval, as stated in the American Heritage Dictionary, 3rd Edition, Copyright 1994:

Frequency.

1a. Number of repetitions of a complete sequence of values of a periodic function per unit variation of an independent variable.

1b. Number of complete cycles of a periodic process occurring per unit time.

1c. Number of repetitions per unit time of a complete waveform, as of an electric current. The number of times the cycles form a repetitive pattern in one unit of length is the frequency of the slot pattern. The number of cycles "C" of the slot undulations superimposed upon the helical path which are present in one revolution around the shaft, is referred to as the cycles per revolution.

The term "biofidelic" has been coined to describe mechanical structures that attempt to duplicate biological structures with high accuracy of fidelity.

Flexible Shaft

The control disclosed flexible shaft provides considerable rotational or torsional stiffness so that it will not store and then irregularly release rotational energy and can be operated both in the forward and reverse directions (clockwise and counter clockwise) with equal effectiveness. The disclosed flexible coupling, for use with the shaft, will also flex, bend or curve while transmitting torque. Since the shaft is a single unit, assembly time is saved.

The shaft of the device of the present invention, indicated generally as 10 as illustrated in FIG. 1 includes an end 14 provided for attachment to a drive means such as an electric or gas driven motor. At the other end 13, of the device 10 includes a connection member 11 providing for attachment to a driven part 15 such as a tool, gearbox, or connecting shaft. The device 10 includes a longitudinal bore 20 spanning from the end 13 to the end 14 thus providing a channel for passage of wires and other instrumentation, as well known in the art and discussed above.

The device 10 includes a slot 32 cut through the wall 22 of the shaft 10, so as to form a serpentine path which extends generally along the path of a spiral around the shaft 10, as shown in Zublin, U.S. Pat. No. 2,515,365, as dotted line 20, FIG. 1.

When employing the flexible shaft 10 for the transmission of power from the driven end 14 to the driven part 15, the serpentine slot 32 along the spiral path permits the device 10 to bend along the longitudinal axis of the device 10. The dovetail configuration of the serpentine slot 32 is composed of teeth 36 and 38. Teeth 36 and 38 will effectively interlock the sections of the dovetail 34 above and below the teeth 36 and 38 and will thereby transmit torque.

Where the device is to be used as a flexible shaft for power transmission, the shaft typically has a diameter less than an inch but may be larger depending upon the specific application. The slot characteristics shown in U.S. Pat. No. 2,515,365 cannot be applied to this application. A one inch or less shaft must have a lower helix angle of the helical path, a higher spiral frequency and fewer cycles of slot undulations about the helical path to provide the required combination of structural strength and flexibility.

Figure 3:
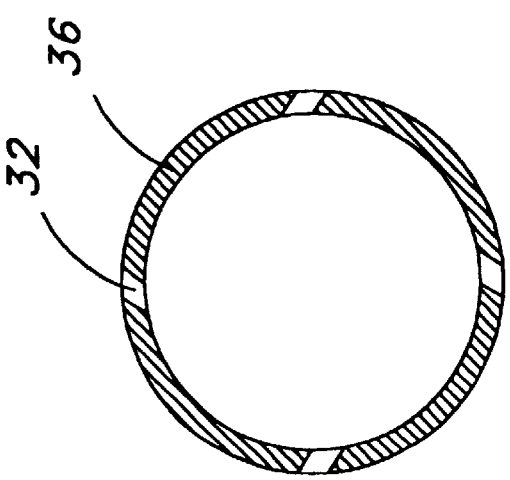
Figure 6A:
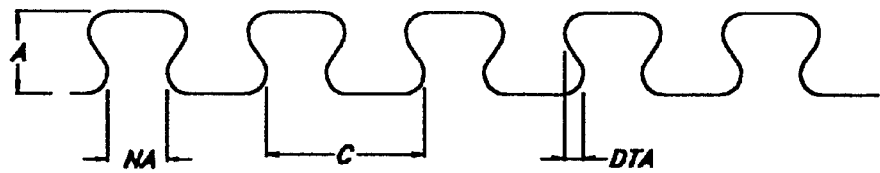
FIG. 6 shows schematic representations of additional spiral slit patterns.
Figure 6B:
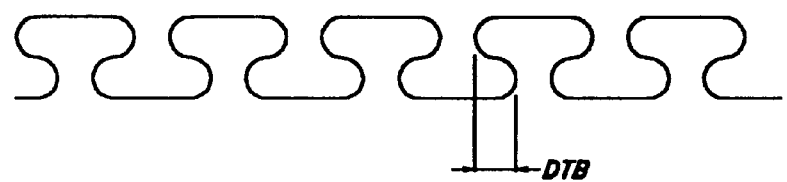
Figure 6C:
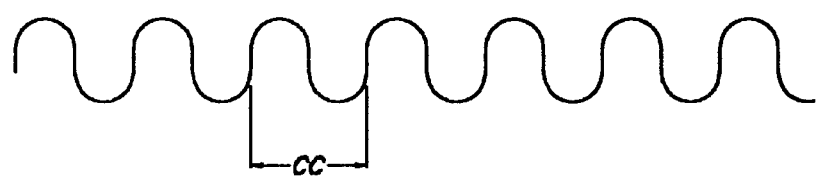
Figure 6D:
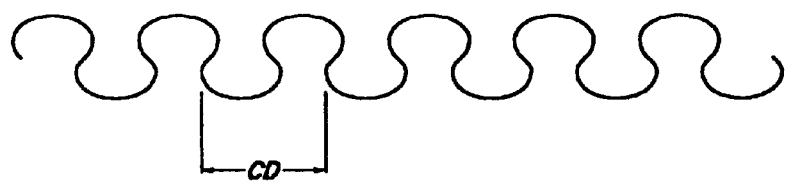
Figure 6E:
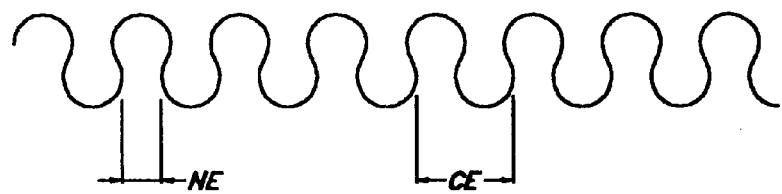
Figure 6F:
Figure 6G:
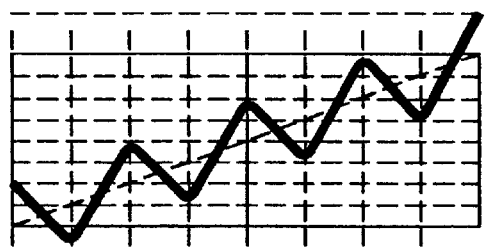
Figure 6H:
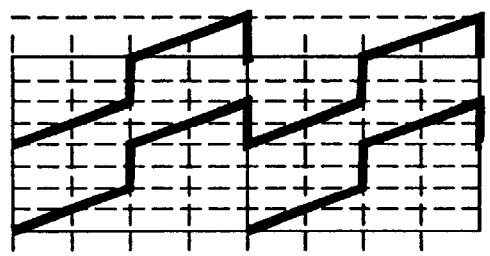
Figure 6I:
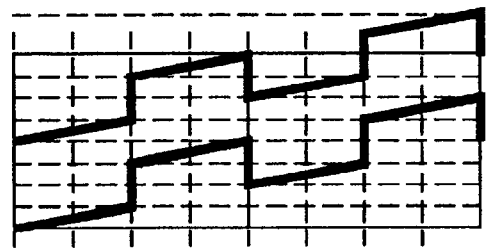
Figure 6J:
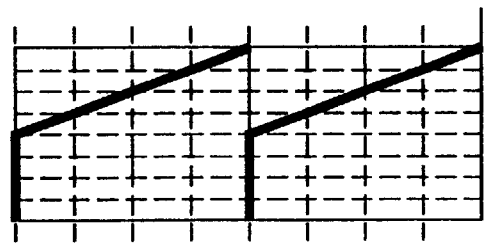
Figure 6K:
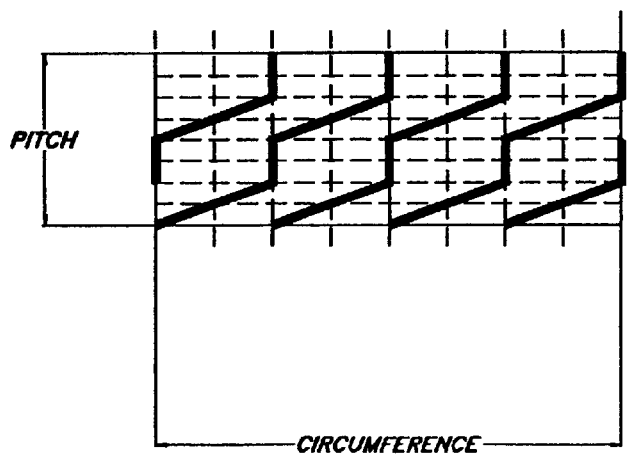

Advantageously, the slot is cut perpendicular to a plane tangent to the outer surface of the shaft as shown in FIG. 3.

Figure 4:
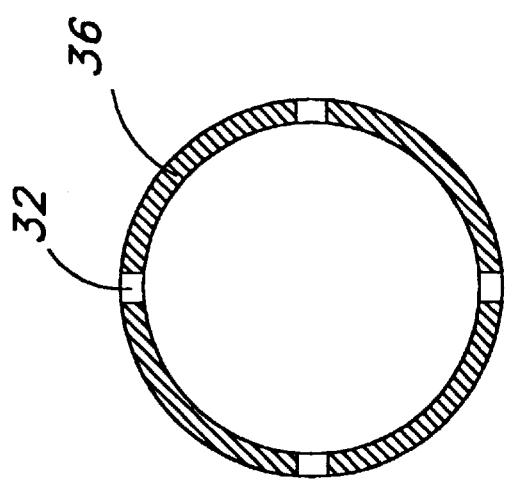
FIGS. 3 and 4 are schematic illustrations showing the angle of the slot.

Alternatively, the slot can be cut at some angle to the longitudinal axis of the shaft and/or the plane tangent to the outer surface, as shown in FIG. 4. The angle can be in the range from zero (perpendicular) to about 75 degrees thereby forming an undercut. Preferably the angle if not perpendicular, is in the range from about 30 to 45 degrees from the perpendicular. The undercut can be formed by cutting offset from the radius, or off-setting from a plane tangential to the surface of the shaft at the slot.

Additionally, in a preferred embodiment, the body of the shaft has a high level of flexibility to facilitate movement around, over or under an obstacle. The preferred embodiment can be constructed in such a manner to provided varying degrees or segments of customized flexibility. Variations in flexibility can most readily be achieved by varying the length of the region that is cut with the spiral slots as well as varying the angle of the slot relative to the long axis of the shaft. Thus, where high flexibility is required a longer length of spiral slot can be used anda greater region length cut. Conversely, where less flexibility is required, a short slot length can be used. Customization enhances the ability to drive the shaft in a straight line where required, to negotiate around, over or under obstacles and/ or to be driven by a rotary power source whose axis is substantially out of line with the axis of the driven part.

Whereas FIG. 1 of Zublin, U.S. Pat. No. 2,515,365 illustrates over six cycles per revolution, for use with four and one half inch diameter drill pipe, in the instant invention, it has been found that shafts of one inch or less requires the use of one to four cycles per revolution depending upon the shaft diameter. Thus, the change in shaft diameter does not result in a proportional change in size of the slot pattern. It has been found that the lower number of helical cycles per revolution produces greater resistance to fracture under torque while providing a less flexible shaft. Most preferably, flexible shafts have a helix angle of less than twenty degrees, in order to produce the required balance between flexibility and structural strength. The range is preferably from about 15 to 20 degrees resulting in a pitch equal to the diameter of the shaft. While the use of a small helix angle, resulting in a higher number of revolutions per unit shaft length, is not preferred unless a very flexible shaft is desired, fewer revolutions per unit length can be used where less flexibility is required. For example, in the varying flexibility flexible shaft, the number of revolutions can be reduced in the relatively rigid regions, as compared to the higher flexibility regions. As shown in FIG. 2, the flexible shaft indicated generally as 100 has the advantage of providing an ability to be routed around, over or under an obstacle, connect to a moving obstacle, provide connection with an unaligned component or to a part in a harsh environment requiring power. The use of a highly flexible shaft 86 permits for ease of guiding the required power to be transmitted to the required part.

The advantage of such a variable flexible shaft, is for a control shaft that must be snaked around different sized obstacles. In sections requiring a smaller radius of curvature, the disclosed shaft can be manufactured for highest flexibility. When variable flexibility is required, the shaft can be cut in restricted areas, or regions, with parts of the shaft remaining uncut. This produces a straight, non-flexible region. The larger the radius of curvature, the less flexible the shaft. The pitch, pattern and length of each region cut can vary within parts of the shaft to provide varying flexibility.

FIG. 1 shows the helix angle, ʘ of the spiral. The smaller the angle, the larger the number of revolutions "R" of the helical path, per inch and the greater the flexibility of the shaft.

A variety of slot patterns are illustrated in FIG. 6 A–K. The patterns are representative of patterns which can be used and are not intended to be all inclusive. As illustrated in FIG. 6A, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 6A and DTB for FIG. 6B. The pattern of 6C, does not provide dovetailing, and requires a helix angle which is relatively small. FIG. D illustrates a segmented, elliptical dovetail configuration with CD indicating the cycle of repetition. In FIG. 6E the ellipse has been rounded out to form a circular dovetail cut with CE indicating the repetitive cycle and the cut pattern of FIG. 6F is a dovetailed frustum. The pattern of FIG. 6G is a sine wave pattern forming the helical path. FIG. 6H is an interrupted spiral in which the slot follows the helical path, deviates from the original angle for a given distance, and then resumes the original or another helix angle. FIG. 6I is the same pattern as FIG. 6H, however in FIG. 6H there are two lead cuts while in FIG. 6I there is a single lead cut. FIGS. 6J and 6K show two dimensions of the same pattern having multiple leads.

Figure 7A:
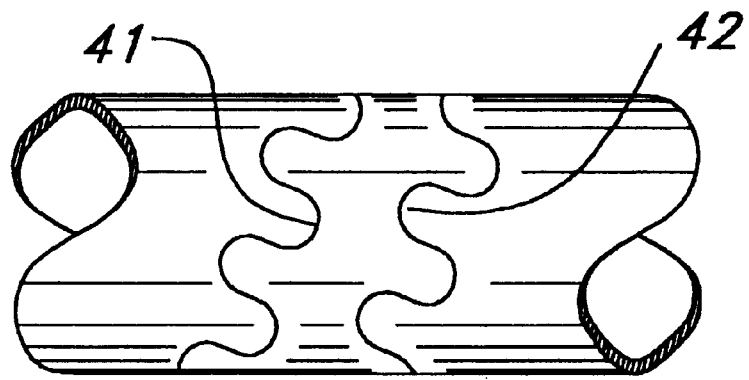
FIG. 7 is a schematic side view showing spiral slits having various numbers of cycles per revolution, that is, different pitches.
Figure 7B:
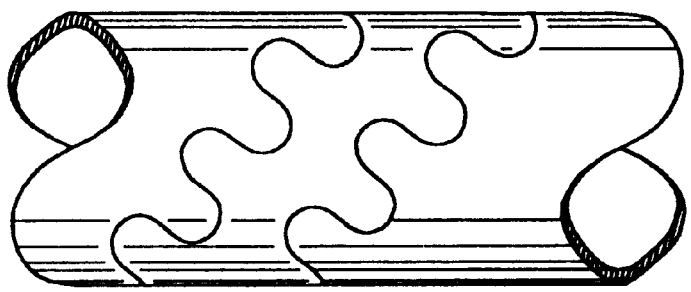
Figure 7C:
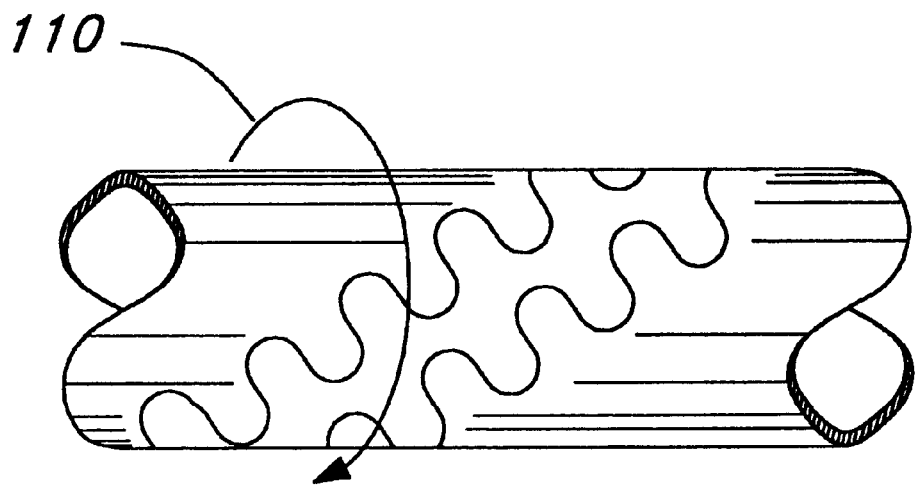

As show in FIG. 7C, rotation in the direction of arrow 110 can open the spiral. The steeper angles of FIGS. 7B and 7C provide progressively greater resistance to opening, even without the dovetailing effect being present. It should be noted that in certain patterns, it is preferred to provide an odd number of cycles per revolution, as shown in FIGS. 7A, 7B and 7C. In this manner the peak point of the cycle 41, is out of phase with the peak point 42 of the next revolution. In these embodiments, when the two points are in phase, the amount of material between the two points is so small as to provide an adequate structural strength. Obviously, the use of a steep helix angle, that is, a very low number of cycles per revolution can be used to provide adequate space between the peak points 41 and 42.

The flexible shaft can be produced by any convenient means. Computer controlled milling or cutting, wire electrical discharge machining, water jet machining, spark erosion machining, and most preferably laser cutting is most conveniently used to produce the desired pattern. The advantages of computer controlled laser cutting are the infinite variety of slot patterns which can be produced, the ability to change the helix angle at any point along the shaft, the variations with respect to slot width, and the overall precision afforded, as compared to conventional cutting mechanisms. The combination of laser cutting with the slot patterns of this inventions, can produce customized shafts having not only a predetermined flexibility, but also predetermined variations in flexibility, while providing substantially uniform characteristics with counterclockwise and clockwise rotation.

Figure 8:
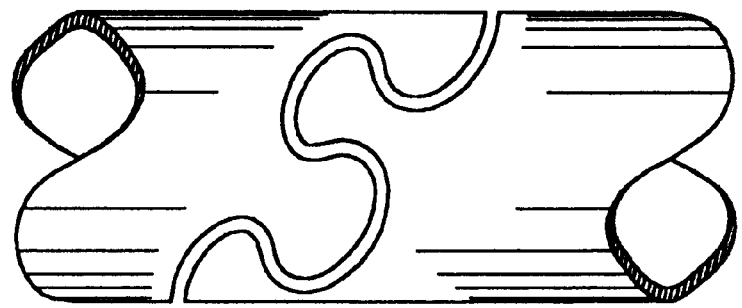
FIG. 8 is a fragmentary side view of the embodiment of FIG. 7, showing the gap formed by the slit.
Figure 9:
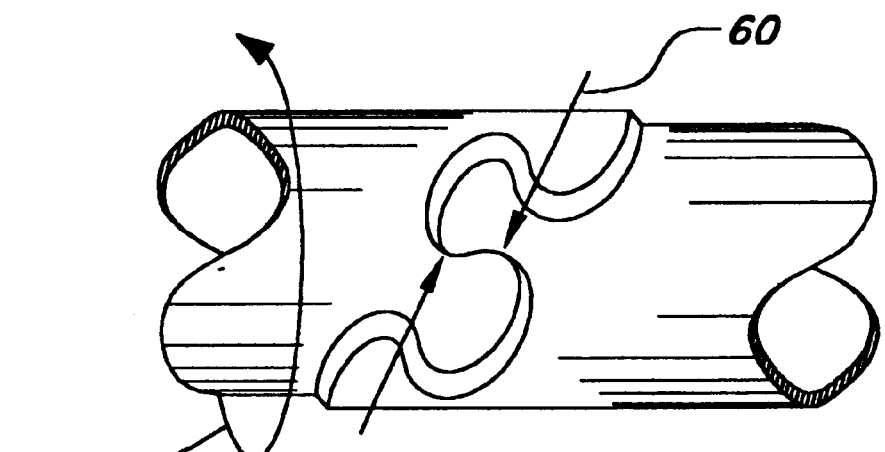
FIG. 9 is a fragmentary side view of the embodiment of FIG. 8, showing a section of the device of the present invention after being torqued in the clockwise direction.
Figure 10:
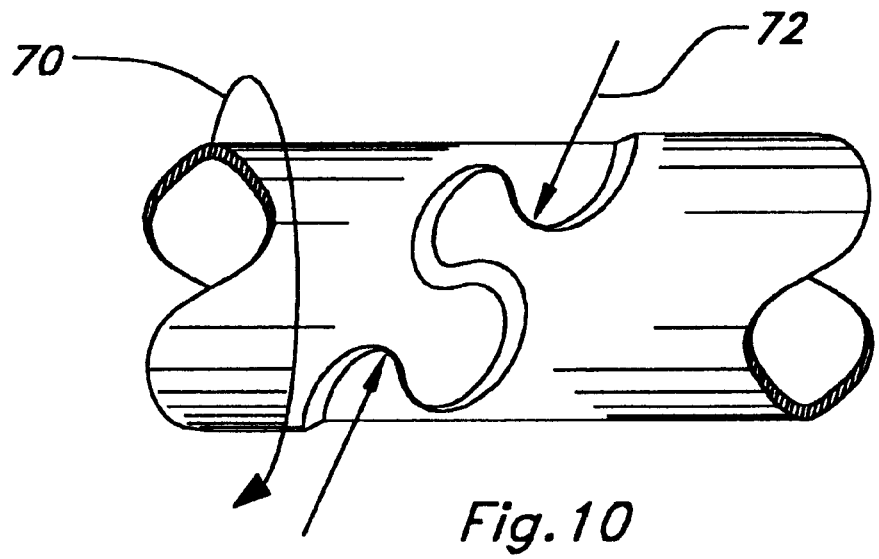
FIG. 10 is a fragmentary side view of the embodiment of FIG. 8, showing a section of the device of the present invention after being torqued in the counterclockwise direction.

The effect of the rotational forces on the flexible shaft is further shown in FIGS. 8, 9 and 10. Rotation in the direction of arrow 62 applies a force in the direction of arrow 62, at the neck region making contact at pont 60. Conversely, rotation in the direction of arrow 70 applies a force in the direction of arrow 70 at the neck region, making contact at point 72.

Figure 11:
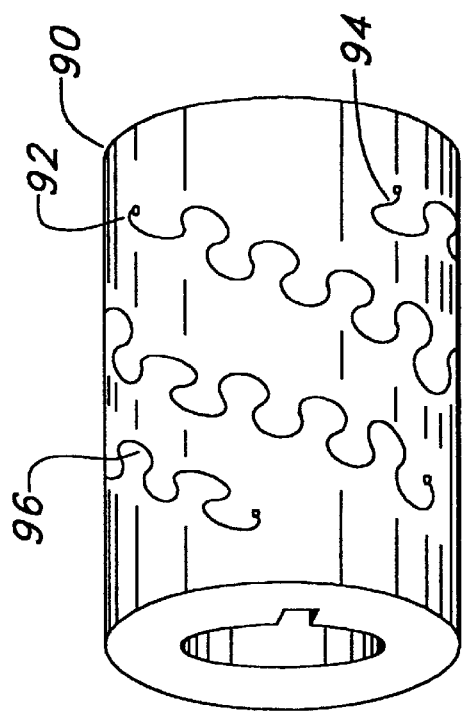
FIG. 11 is a perspective view of a flexible coupling using the spiral slit of the present invention and showing a plurality of spirals slots.

FIG. 11 shows the design of a flexible connector 90 which can be inserted between, for example, a rotary power supply and an inflexible or moderately flexible shaft. The flexible connector can be used to provide power transmission between misaligned parts as previously described. In this embodiment, advantageously, a plurality of slots 92, 94 and 96 can be used, as shown in FIG. 11.

FIG. 2 shows the design of a flexible shaft or connector 100 in which an elastomer or otherwise flexible material is interposed within the slot 102 to further enhance the flexibility of the shaft and to alter the torsional response or stiffness of the member. The elastomer can be used as a shock absorbing or cushioning member. To facilitate manufacture, to provide protection of the tubular member, to provide a fluid conduit or for other reasons, the elastomer can encapsulate the entire shaft or coupler, thus forming a tubular construction 104.

Figure 12:
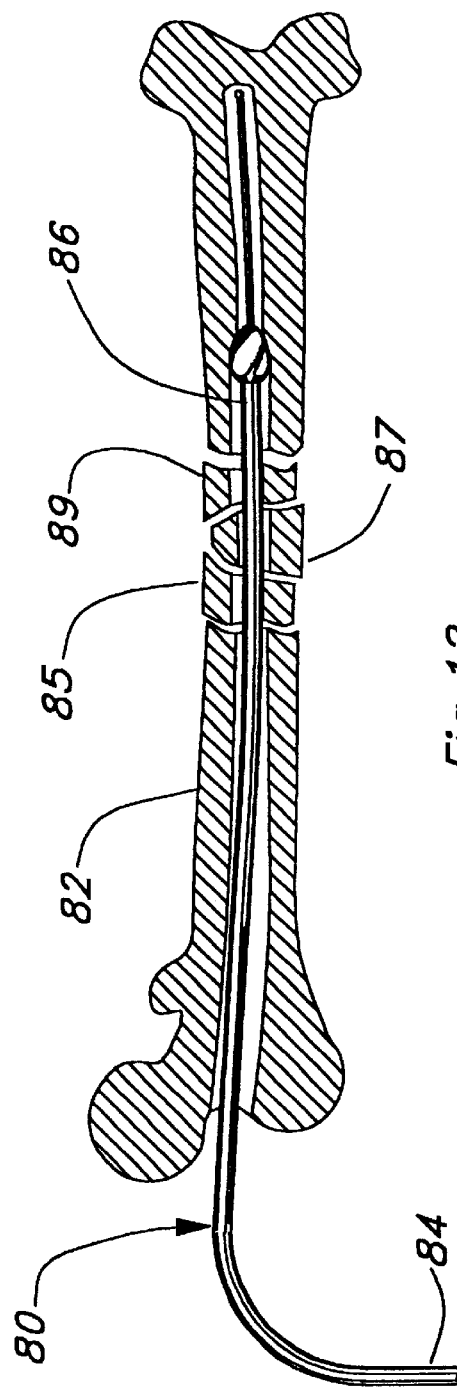
FIG. 12 is a schematic and cut away view of the shaft employed in reaming a medullary canal of a femur.

In a preferred embodiment of the invention the flexible shaft is to be used as a flexible shaft for reaming the medullary canal of bones, the shaft must have a diameter less than that of the reamer which typically has a cutting diameter of about two tenths of an inch up to less than three quarters of an inch. The spiral pattern shown in U.S. Pat. No. 2,515,365 cannot be applied to this application. The three quarter inch or less shaft must have a higher spiral frequency (lower helix angle) and fewer superimposed slot cycles to provide the required combination of structural strength and flexibility. As show in FIG. 12, during the reaming of the medullary canal of the femur it is preferred that the shaft be able to flex, up to about 45 degrees. The flexible shaft indicated generally as 80 has the advantage of providing an ability to ream the medullary canal of the femur 82 with the driven end 84 of the shaft at roughly a right angle to the axis of the femur. The use of a highly flexible reamer end 86 permits for ease of guiding the reamer through the bone fragments 85, 87 and 89.

Spinal Unit

The ability to vary the stiffness properties of the cylinder through adjustment of the helical pattern enables the device to be used as a spinal unit for anthropomorphic test devices used in crash and/or ejection system tests. The human operators of automobiles and aircraft are subjected to severe accelerations during crash or ejection situations. Evaluation of the effects of these events on the human body is important in designing safe and effective restraint and/or ejection systems to minimize occupant injury. In order to provide accurate data, the response of the anthropomorphic test devices simulated crashes or high acceleration events are used.

The development of test dummies demonstrates that they have been designed primarily for applications in automobiles. One of the main concerns in automobile crashes is the response of the torso to impacts from the forward and lateral directions. Dummies designed for automobile crashes are not, however, truly adequate for ejection seat testing, because ejection seat dummies are subjected to sudden vertical accelerations as well as to horizontal acceleration. Anthropomorphic models used in ejection seat testing are commonly referred to as "manikins" instead of dummies, because these models are much more sophisticated representations of the human body. Test manikins have been developed specifically for ejection seat testing by the Armed Services.

Figure 13:
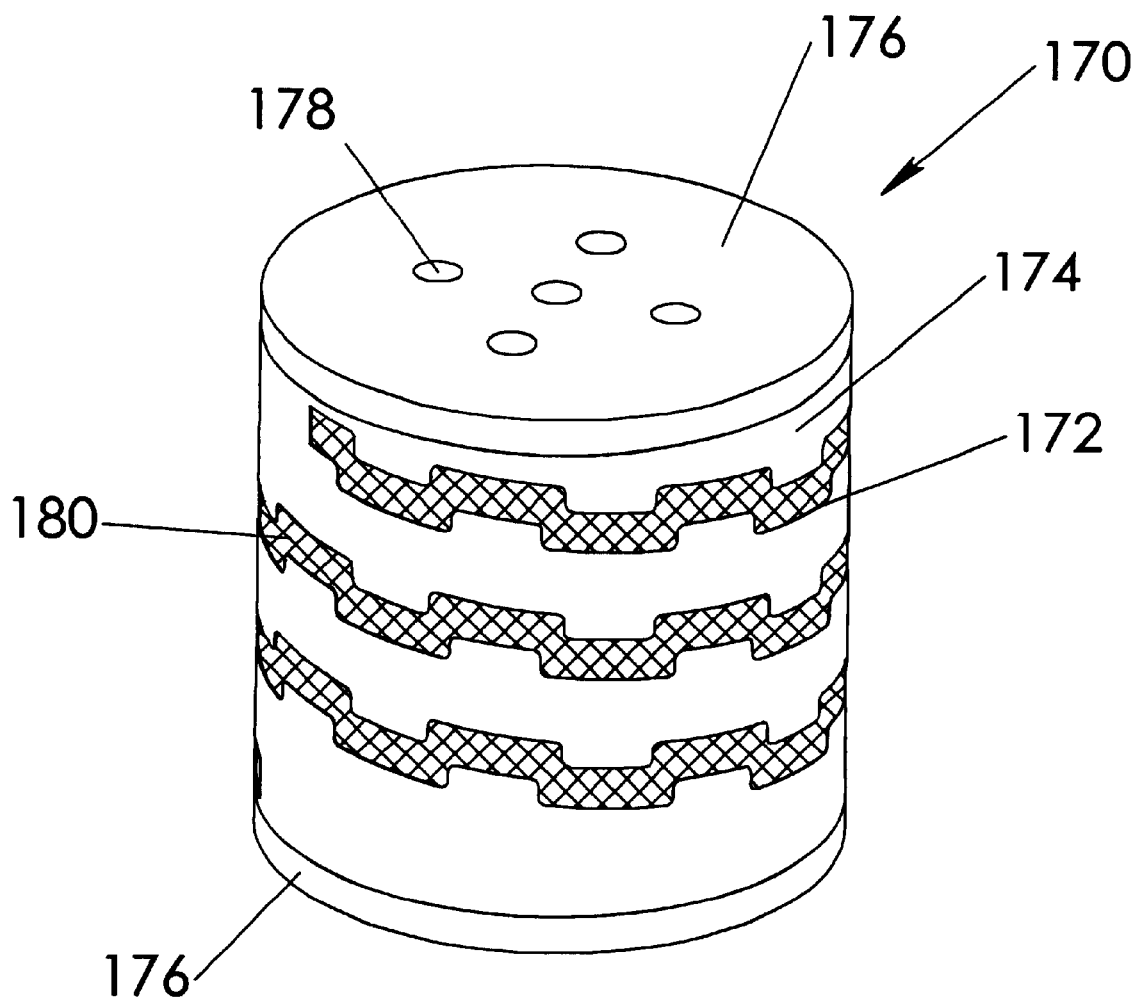
FIG. 13 is a perspective view of an anthropomorphic spinal unit for incorporation into crash test dummies and manikins.

The disclosed spinal units possess, at least in one direction, the stiffness properties of a human spine segment enabling it to be used in creating equipment designs for protecting occupants of vehicles in crashes or in sudden positive or negative accelerations. The spinal unit simulates the response of human occupants' in testing for the effectiveness of protective equipment by providing a biofidelic manikin spine segment (lumbar, thoracic and/or cervical) that faithfully reproduces human-like responses in ejection seat and vehicle crash tests. This assists researchers in identifying and eliminating the cause of spinal injuries. The spinal unit 170, as shown in FIG. 13, can be retrofitted into existing anthropomorphic test dummies used in vehicle safety tests. In addition to automotive crash testing, aircraft crash test evaluation and aircraft ejection seat response would benefit from the disclosed spinal unit by providing the biofidelity with respect to the human response in the appropriate acceleration directions.

In this application a non-interlocking slot 172 as described in FIG. 6, with a wide gap, is cut into a cylindrical shaft 174 bounded by end plates 176. The slot 172 is filled with a resilient elastomer 180 such that the combination of the design properties of the unit, such as the slot pattern, the slot width, the ratio of the slot amplitude to the slot pitch, the number of helix slots, the thickness of the cylinder wall, the diameter of the shaft, the elasticity of the shaft material, and the elasticity of the elastomer material, will determine the axial, bending, and torsional response of the spinal unit 170 to respective loading application. The diameter of the spinal unit 170 must be compatible with existing spinal units for retrofit into existing anthropomorphic test dummies used in both automobile and aircraft safety tests. The diameter of the attachment mechanism is typically in the range of 3.5 to 4.5 inches although the diameter of the flexible segment may be greater or less than the attachment diameter. The endplates 176 are rigidly fixed to the cylindrical shaft 174 and contain holes 178 to provide attachment to existing anthropomorphic test dummies used in either automobile and aircraft safety tests.

The spiral pattern shown in U.S. Pat. No. 2,515,365 to Zublin cannot be applied to this application as the slot gap and configuration described by Zublin would not provide the necessary tri-axial stiffness to duplicate the stiffness and displacement of the human spinal segment being modeled. The slot gap described in the embodiment must be wider and filled with an elastomer to provide the stiffness characteristics of the human spine segment being modeled. The ratio of the slot width to the pitch must be greater than described by Zublin.

Vertebral Body Replacement Implant

An important aspect of this invention lies in providing a prosthesis for total replacement of a vertebral body and adjacent discs that will provide the flexibility and stiffness of the resected vertebra and, when properly in place, provides a stress environment at the prosthesis/bone interface similar to normal in vivo conditions. Specifically, the invention can be utilized to produce an implant in which the normal ranges of movement are preserved, the prosthesis permitting limited longitudinal flexure, slight compression and expansion, and even a limited degree of torsional movement that at least approximates a normal vertebral response.

Figure 14:
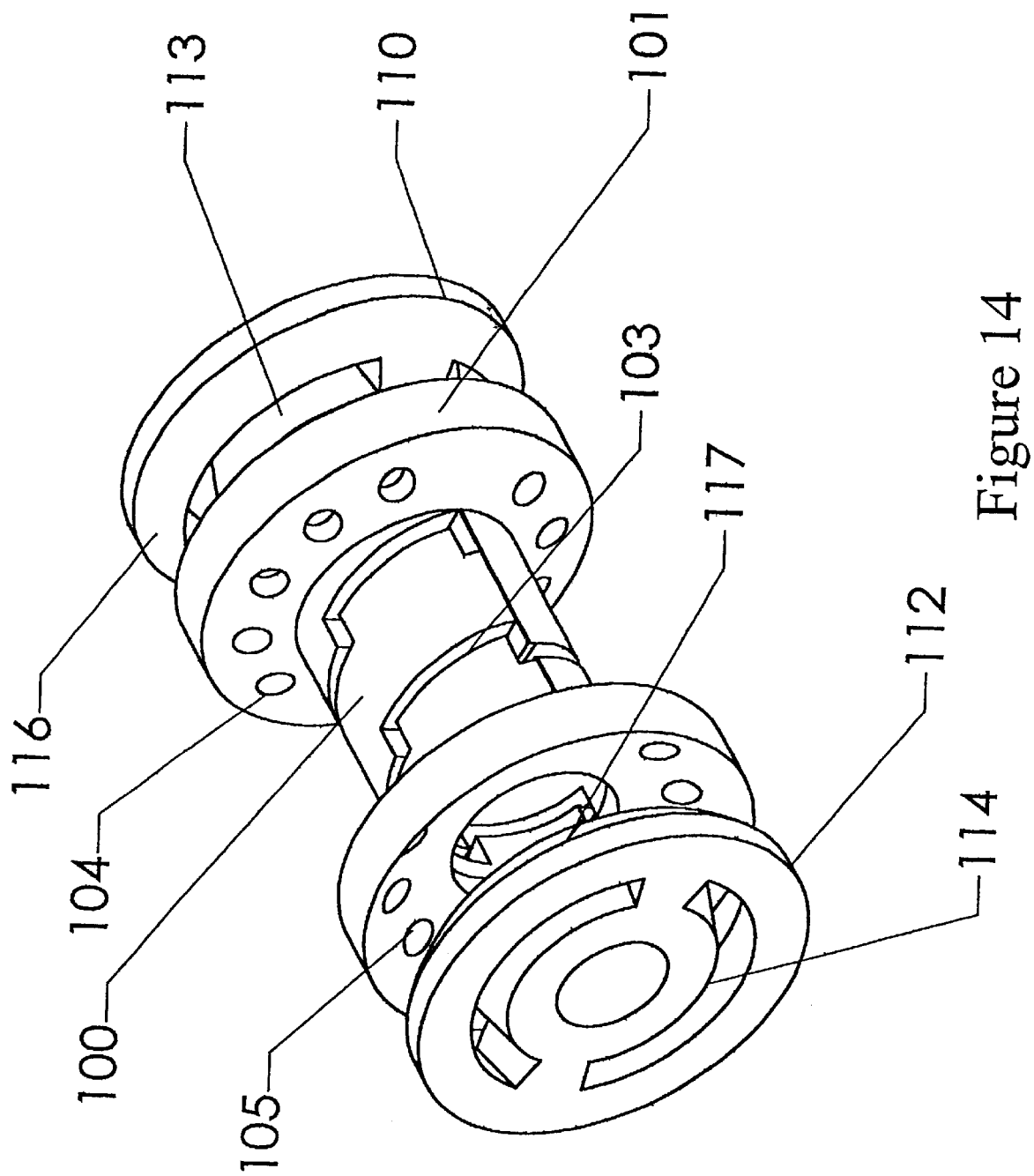
FIG. 14 is a perspective view of a vertebral body replacement implant to replace a diseased or damaged vertebra.
Figure 15:
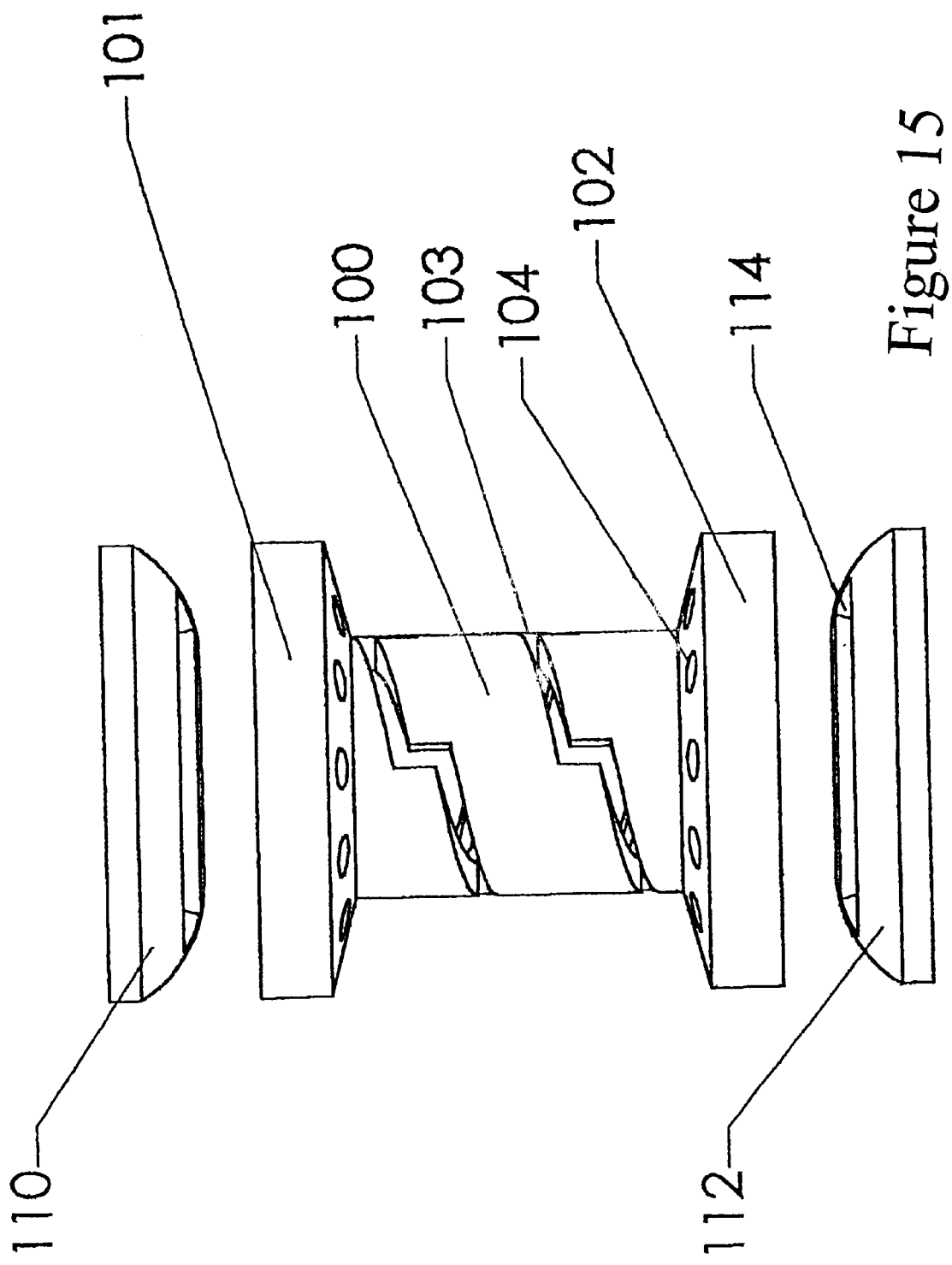
FIG. 15 is a side view of the vertebral body replacement implant of FIG. 14.

In FIGS. 14 and 15 the helical cylinder is used as a central section of a vertebral body replacement implant formed of rigid biocompatible material such as, for example, stainless steel or titanium, for use in the cavity left after removal of a diseased or defective vertebra in a human or animal spine. The central section 100 is formed with an upper endplate 101 and lower endplate 102 for attachment to the adjacent vertebra and to engage spacer/alignment discs. The central section 100 has a spiral, helical slot 103 machined in the body. The slot 103 configuration and properties of the cylindrical body 100 are designed to duplicate the stiffness, within a reasonable allowance, of the vertebra and adjacent intervertebral disc resected. The helical slot 103 cut into the central section can have an elastomer or otherwise flexible material interposed within the slot 103 to further enhance the flexibility of the central section 100 and to alter the torsional response or stiffness. The elastomer can be used as a shock absorbing or cushioning member. To facilitate manufacture, to provide protection of the tubular member, to provide a fluid conduit or for other reasons, the elastomer can encapsulate the entire central section 100, thus forming a tubular construction.

The upper and lower endplates 101 and 102 are configured to provide anchoring with the adjacent vertebra by means of screws or other means. The endplates 101 and 102 contain holes 104 and 105 respectively, through which the screws or pins can be passed into the adjacent vertebra. The end surfaces of the endplates 101 and 102 can be of concave or convex shape to mate with alignment discs 110 and 112 that are superimposed between the implant and the adjacent vertebra. The screws or fixation pins would pass through the implant endplates 101 and 102 and the respective alignment discs 110 and 112 to rigidly fix the implant to the adjacent vertebra and allow for the natural curvature of the spine.

In order to compensate for the varied height of the vertebra from individual to individual, the alignment discs 110 and 112 are manufactured in various thicknesses. In this way, the more complicated implant itself can be manufactured in a limited number of sizes with the smaller variations being picked up by the alignment discs 110 and 112. The alignment discs 110 and 112 are provided with slots 113 and 114 respectively to enable additional adjustability. The screws pass through the holes 104 and 105, through the slots 113 and 114 and into the adjacent vertebra. The mating surfaces 116 and 117 of the alignment discs 110 and 112 are configured to nestle within the adjacent endplate 101 and 102. Preferably these surfaces are concave and convex to appropriately align and provide for maximum adjustability.

It is to be understood that the surface of the disc interfacing with the vertebra can be foraminous to facilitate and promote bone in growth. As well known in the art, sintered metal surfaces have been found particularly effective for that purpose. While a detailed discussion is believed unnecessary, it will be appreciated that the attachment screws are particularly important for initial fixation and for immobilizing the implant with respect to the adjoining vertebrae so that bone in growth may ultimately occur, at which time the in growth becomes a major factor in maintaining fixation. Another major factor in achieving and maintaining fixation is believed to be the limited yieldability of the prosthesis which, by mimicking the action of the replaced components, reduces the stresses at the bone/prosthesis interfaces.

Further applications and usage of the invention can be thought of which entails the technology of the invention requirement of a device which requires specific multi-directional stiffness characteristics. Other uses for the disclosed tubular structure having certain stiffness characteristics as required by the application will be understood by those skilled in the art when addressed in conjunction with the instant disclosure.

What is claimed is:

1. A method of reaming the medullary canal of bones, comprising
   a. connecting a first section of a flexible shaft to a power source transmitting rotational motion
   b. connecting a third section of a flexible shaft to a medullary bone canal reamer;
   c. transmitting rotation from said power source to said reamer through a flexible shaft center section having a slot of substantial length and width to form a plurality of teeth having complimentary recesses on opposing sides of said slot and extending in a generally helical path around and along the tubular member
   d. reaming said medullary bone canal by rotating said reamer in the clockwise and counterclockwise direction, wherein said slot width is sufficient to form an unbound joint permitting limited movement in any direction between the teeth of the recesses thereby providing limited flexibility in all directions upon application of tensile, compressive, and/or torsion forces to said shaft.

2. The method of claim 1, further comprising the step of limiting flexibility by using teeth in the form of a serpentine wave.

3. The method of claim 1 further comprising the step of limiting flexibility using teeth in the form of a square wave.

* * * * *